United States Patent [19]
Fiore

[11] Patent Number: 5,741,222
[45] Date of Patent: Apr. 21, 1998

[54] ANKLE JOINT SUPPORT

[76] Inventor: Russell D. Fiore, 6 Red Chimney Dr., Lincoln, R.I. 02865

[21] Appl. No.: 539,625

[22] Filed: Oct. 5, 1995

Related U.S. Application Data

[63] Continuation-in-part of Ser. No. 258,221, Jun. 10, 1994, abandoned.

[51] Int. Cl.$^6$ .................................................. A61F 5/00
[52] U.S. Cl. ...................... 602/27; 602/6; 602/23
[58] Field of Search ................... 602/23, 27, 62, 602/65; 128/882, 892

[56] References Cited

U.S. PATENT DOCUMENTS

| | | | |
|---|---|---|---|
| 4,527,556 | 7/1985 | Nelson | 602/27 |
| 4,638,794 | 1/1987 | Griser | 602/27 |
| 4,665,904 | 5/1987 | Lerman | 602/27 |
| 4,719,926 | 1/1988 | Nelson | 602/27 |
| 4,724,847 | 2/1988 | Nelson | 602/27 |
| 4,727,863 | 3/1988 | Nelson | 602/27 |
| 4,825,856 | 5/1989 | Nelson | 602/27 |
| 4,834,078 | 5/1989 | Biedermann | 602/27 |
| 4,844,058 | 7/1989 | Vogelbach | 602/27 |
| 4,862,900 | 9/1989 | Hefele | 602/27 |
| 4,878,504 | 11/1989 | Nelson | 602/27 |
| 4,960,135 | 10/1990 | Nelson | 602/27 |
| 4,998,537 | 3/1991 | Rau | 602/27 |
| 5,000,195 | 3/1991 | Neal | 602/27 |
| 5,007,417 | 4/1991 | Bender | 602/27 |
| 5,014,691 | 5/1991 | Cuerman et al. | 602/27 |
| 5,027,501 | 7/1991 | Grim | 602/27 |
| 5,067,486 | 11/1991 | Hely | 602/27 |
| 5,199,941 | 4/1993 | Makinen | 602/27 |
| 5,366,439 | 11/1994 | Peters | 602/27 |
| 5,472,411 | 12/1995 | Montag et al. | 602/23 |
| 5,527,629 | 6/1996 | Riethofer | 602/27 |
| 5,620,413 | 4/1997 | Olsen | 602/65 |

FOREIGN PATENT DOCUMENTS

9421201   9/1994   WIPO ......................... 602/27

Primary Examiner—Richard J. Apley
Assistant Examiner—Kim M. Lee
Attorney, Agent, or Firm—Robert J. Doherty

[57] ABSTRACT

An ankle support including a first member in the form of an envelope for enclosing a major ankle portion and which holds a relatively separate stiff brace in position with respect to the wearer's ankle such that portions of the brace are respectively generally forward and above the wearer's malleoli so as to simultaneously reduce ankle eversion and inversion.

10 Claims, 7 Drawing Sheets

FOOT INVERSION TEST

FIG. 9A

FOOT EVERSION TEST

FIG. 9B

RANGE OF ANKLE DORSIFLEXION

FIG. 9C

RANGE OF ANKLE PLANTER FLEXION

FIG. 9D

THE BONY ANATOMY OF THE FOOT AND ANKLE
(LATERAL ASPECT)

FIG. 9E

THE BONY ANATOMY OF THE FOOT AND ANKLE
(MEDIAL ASPECT)

ANKLE JOINT SUPPORT

BACKGROUND AND OBJECTS OF THE INVENTION

This application is a continuation-in-part of U.S. patent application Ser. No. 08/258,221 filed Jun. 10, 1994, now abandoned.

This invention relates to ankle supports that may be used for both athletic and medical purposes. Many supports of this general nature are known and specifically include those disclosed in the following U.S. patents: U.S. Pat. No. 4,527,556 issued Jul. 9, 1985 and U.S. Pat. No. 5,038,762 issued Aug. 13, 1991. The '556 patent is illustrative of an envelope or lace-up type support which provides a general stiffening support to the ankle joint while the '762 patent is illustrative of an ankle support known as a rigid support which are held in place with straps and the like.

A general theory of both such braces is to attempt to restrict the lateral movement of the joints of the ankle and rear foot joint, that is, its lateral side to side rotational movement in the frontal plane, about the major bones and joints of the ankle and foot to protect the ankle joint ligaments or other injured joint portions from further tearing, rupturing or overstretching. In addition, such braces should at the same time permit adequate up and down or forward and rear motion of the ankle in the sagittal plane about the major bones and joints of the lower leg, ankle and foot in order to provide necessary mobility for the wearer to move about in a substantially normal manner. In other words, it is desirable to limit inversion and eversion ankle motion wherein inversion (FIG. 9A) is lateral movement towards the opposite leg or mid line and eversion (FIG. 9B) is the lateral movement away from the other leg or mid line and still permit dorsi flexion (FIG. 9C) (upward movement of the toe portion of the foot) and plantar flexion (FIG. 9D) (downward movement of the toe portion of the foot) with respect to the ankle.

With respect to the above-mentioned patents, the '556 patent provides a general stabilizing effect on the entire ankle while the '762 device provides adequate lateral resistance with respect to inversion but little, if any, resistance from the opposite lateral movement or eversion.

Accordingly, it is an object of the present invention to provide a support which provides a general support to the ankle which yet additionally essentially prevents both inversion and eversion thereof yet permits adequate up and down flexion such that the wearer does not lose desirable mobility.

These and other objects of the present invention are accomplished by an ankle joint support adapted to be worn over the foot of a human so as to support the ankle and ankle joint thereof comprising a first member defining a cavity for the receipt of the foot and having a generally U-shaped body having a bottom and opposed sides adapted to fit around the bottom and opposed sides of the human foot and defining a toe opening at the front thereof and a heel opening at the rear thereof and a second member in the form of a relatively rigid sheet-like generally U-shaped brace, said brace having a pair of upwardly rearwardly extending arms and a connecting base portion, said second member fixedly positioned with relation to said first member with said second member base portion positioned to conform to that portion of the envelope passing underneath the posterior arch of the wearer's foot with said arms upwardly extending from said base portion to points generally forward of both the inner and outer malleolus of said wearer and means associated with said first member for releasably retaining said support on the ankle of said wearer.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DETAILED DESCRIPTION OF THE INVENTION

Referring now to the drawings and particularly FIGS. 1 through 5, the overall structure of the support 10 is shown. In essence, the support forms an envelope, i.e., a glove or sock, which fits over the major portions of the wearer's foot and from which the toes and heel project. Accordingly, the support 10 includes a generally U-shaped body 12 having opposed inside and outside sides 14 and 16 respectively and a lower connecting portion 18.

As shown, the body 12 is formed from three separate material sections including a first section 20, an inner or second section 22 which is laced or otherwise connected in face to face relationship therewith and a third or outer section 24. In this regard, the construction of the present envelope may take the form of that shown in the previously discussed U.S. Pat. No. 4,527,556 and for that purpose the descriptive portion of that patent is hereby incorporated into the present Specification by specific reference. Generally, the sections are formed of a reinforced thin flexible plastic coated fabric material (i.e., vinyl coating) which is strong, durable and easily washable or a similar type of material or fabric that functions in the same manner.

As shown in the drawings, the first section 20 and to some extent the second section 22 which may be co-extensive therewith and thus suitable for forming an interior pocket 25 between such sections or layers 20, 22 as will hereinafter be more fully explained is configured to conform generally to the human lower leg or ankle joint and preferably be symmetrical such that it will conform to either the wearer's left or right foot. The sections 20, 22 extend around the rear or Achilles tendon foot portion and thence forwardly where they terminate in opposed forward sections and edges 26 and 27 respectively which are laterally spaced apart. The space 28 between the forward edges 27 accommodates a knit elastic fabric member 30 respectively attached by any suitable means such as sewing to the opposed sections 20, 22. A conventional shoe-type tongue could be used in place of or in addition to the fabric member 30. The space forward of the aforementioned connection with the flexible fabric member 30 is shown provided with a series of eyelet openings 32 either with or without grommets 34 such that a lacing 36 may be utilized to hold the forward portions of the first and second sections 20, 22. Other connection means may also be utilized including snap fasteners or Velcro fasteners.

Such forward sections, in essence, form flaps which are then laced in a conventional manner. The third or outer section 24 can be suitably attached to outer sections of the first section 20 as depicted to provide space between such sections for placement of ice packs and the like. Such third section 24 is provided with a pair of flaps 40 similar to flaps 27 for interconnection therewith. It should be pointed out that the outer section 24 may be removed if its features are not required. Also, the inner section 22 may be removed as long as adequate padding is provided on the interior surface of the envelope so that the wearer is comfortable and some alternate structure to pocket 25 is afforded.

The front of the envelope is provided with toe opening 42 and the rear of the envelope is provided with a heel opening 44. In addition, the rear edges of the first, second and third sections are provided with an elastic fabric 31 spanning the space between the opposed sides thereof similar to the fabric 30 in the front position thereof and providing some measure of protection for the Achilles tendon in addition to its fit function in accommodating slight foot size variations. It is also proposed to provide the envelope and thus the support in varying sizes. In addition, the upper opposed edges of the rear heel opening 44 are preferably provided with a stiffening connector bridge portion 46 which may be formed by an added strip of plastic coated material and which functions to some extent to join the envelope sections together so that they function somewhat more as a unit for a purpose which will hereinafter be more evident. The composite result is an envelope suitable for purposes of enveloping the lower leg or ankle portion of a human needing support thereof in the intended fashion and suitable for receiving the second member of the present invention which is in the form of a brace 50.

Such brace is preferably formed from a relatively rigid plastic material such as SURLYN, polyethylene, polypropylene or other suitable materials including metal yet is of relatively thin-walled construction such that it may be received within the pocket 25 formed between the first and second sections 20 and 22 and positioned in overall relationship with the structural aspects of the wearer's foot for the intended accomplished purposes of the present invention. In other words, the brace 50 should be thin enough so that it conforms to the shape of the user's ankle and foot and does not interfere with the use of orthotic devices and does not interfere with the wearer's comfort yet thick enough to convey a rigid support to achieve the intended restraint to the opposed lateral movement directions of the foot. A specific brace example found to be satisfactory utilized a clear SURLYN material No. 8940 sold in sheet form by Bixby Int. Corp. of Newburyport, Mass. 01950 that was 0.0625 inches thick and of a height of about 8 inches. The width of this specific brace example varied from about 1 inch at the center to about 1½ inches at its top and about 1¾ inches at its bottom. This specific material (SURLYN) in such thickness and shape inherently has a relatively high degree of flexibility but yet when confined within the envelope pocket as previously described imparts the necessary rigidity to the overall supports other materials that may be used for the braces should also impart such overall resultant characteristics to the support.

Figures 9A, 9B, 9C, 9D:
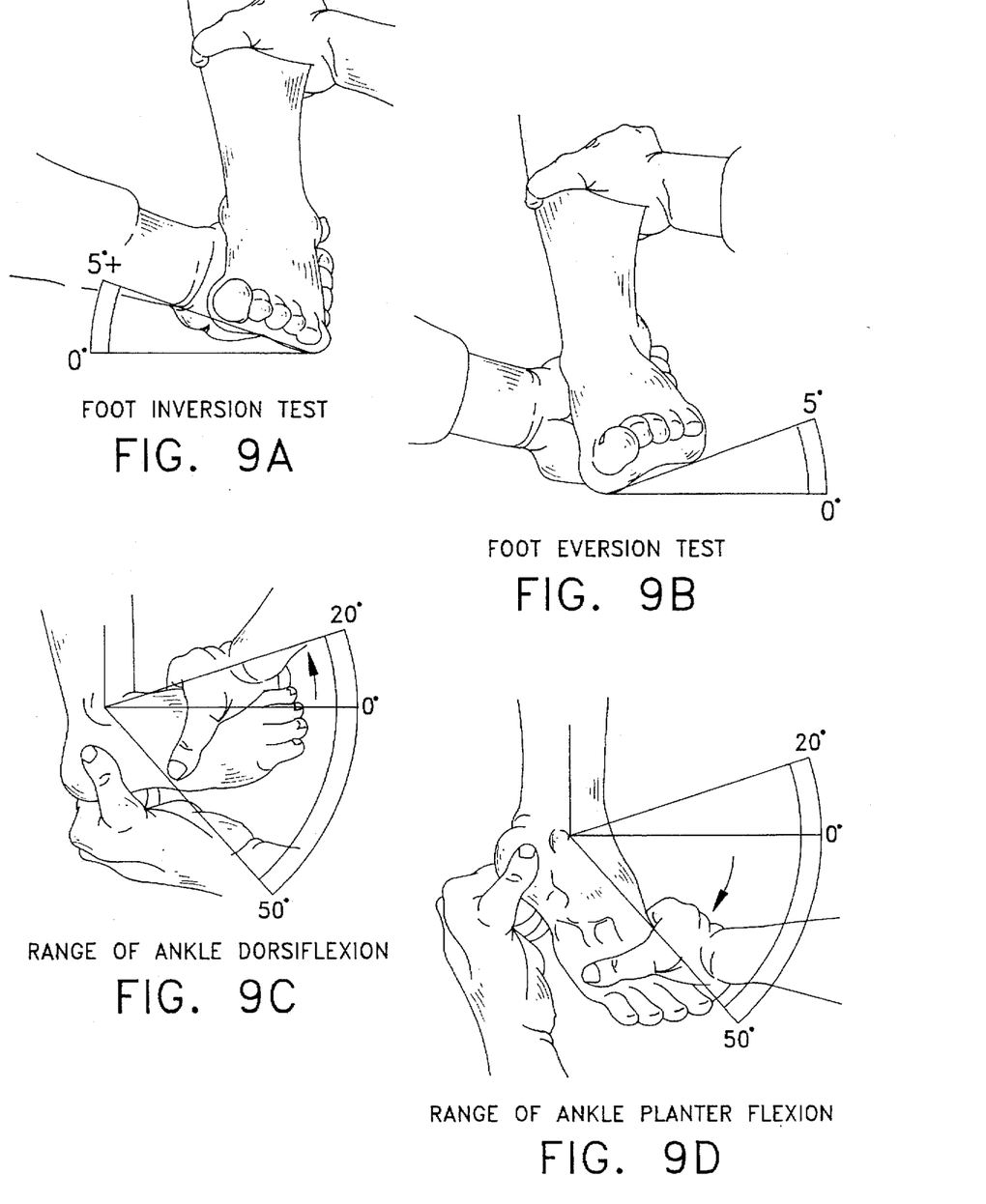
FIGS. 9A through 9F are stylized views of the bones and movements of the human foot.
Figure 9E:
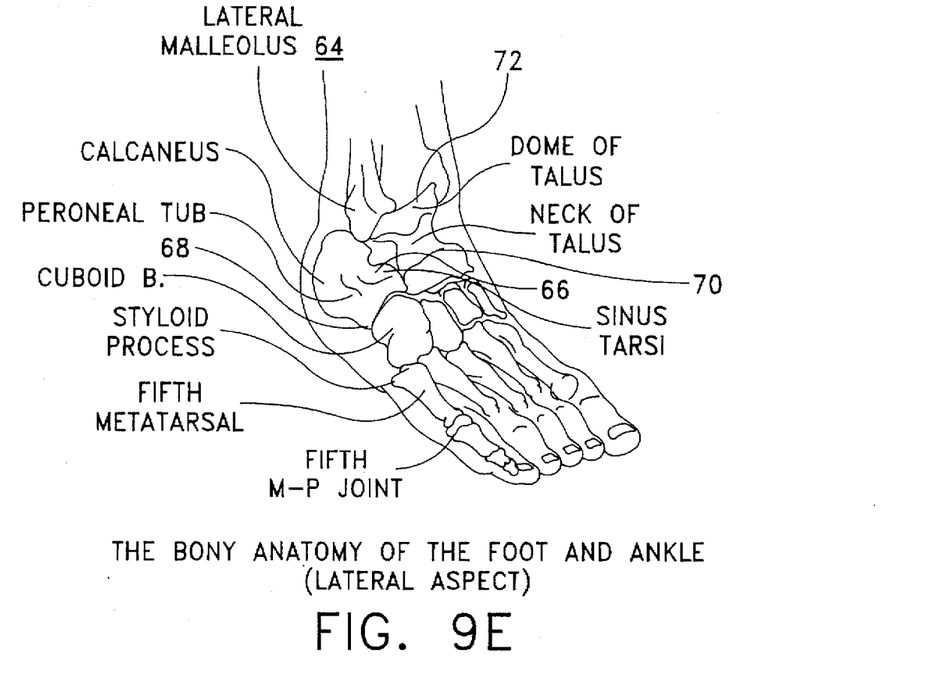
Figure 9F:
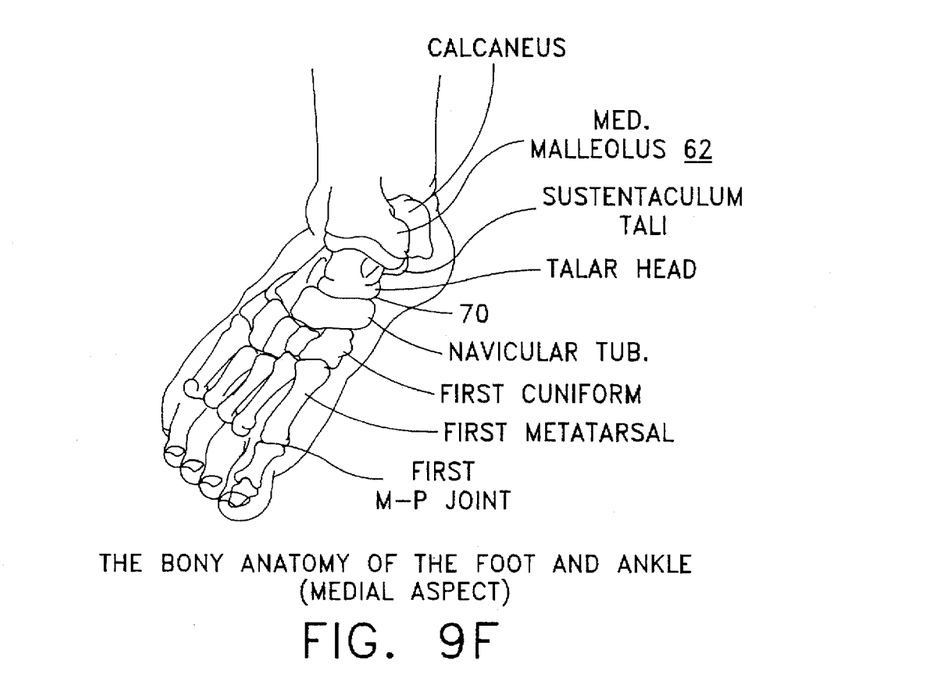

Thus the brace 50 takes the form of an overall U-shaped configuration having opposed arms 56 and 58 and a connecting bottom portion 60 all preferably of integral construction. The arms 56 and 58 extend initially upwardly and generally forward from the connecting or bottom portion 60 to points adjacent the malleoli and thence rearwardly and upwardly such that when positioned in the pocket 25 they are disposed generally forwardly of both the inside and outside malleolus, that is, the medial and lateral malleolus 62, 64 respectively. Such position is important in that a major portion of the inversion and eversion movements occur in the anterior subtalar 66, calcaneo cuboid 68 and the talo navicular joints 70 which are all located anterior to the medial and lateral malleoli. Thus for the explanatory and demonstration purposes of this invention, a lateral line drawn between the malleolus roughly approximates the pivot line or point in which the ankle joint demonstrates lateral turning motion in opposed directions with respect to the lower leg portion. Actually the movement of the various joints of the ankle is far more complex. The diagrams shown in FIGS. 9 are helpful to demonstrate the types motion that are afforded. Wherein relative combined rotational movements between the talus and calcaneus, talus and navicular and the calcaneus and cuboid enables the aforementioned lateral motions which are desired to be constrained by the device of the present invention and relative motion between the talus and tibia 72 enables to a major degree the upward and downward flexion of the foot which to some extent is desirable so that the patient wearing the support 10 of the present invention has necessary mobility without injuring or re-injuring ligament or causing other damage brought on by the undesirable inversion and eversion ankle motions. Preferably a sheet of dense plastic or rubber foam or similar padding material 48 is inserted between the first and second envelope sections but in any event in a position such that the brace 50 overlies such on either side of the envelope. The padding material 48 does not necessarily conform to the shape and extent of the pocket 25 but does underlie such at least in an area including the malleoli. Such padding material 48 is provided on both sides of the envelope as well to insure comfort.

It is thus been found that by providing a sufficiently rigid brace 50 and positioning such forwardly of the malleoli that the desired reduction of inversion and eversion is accomplished. With respect to the term forwardly as used herein, it is meant that the portions of the brace 50 adjacent the malleoli are positioned generally and to a major extent forwardly thereof. The term forwardly is not meant, however, to preclude some coverage of or overlapping of the malleoli by the brace so long as the brace in those adjacent areas is located to a large or major extent in front of the malleoli. Thus by holding such brace in position by, in effect, locking its arms 56 and 58 to upper ankle portions by the fixation of the envelope body 12 on the ankle by lacing, the foot is effectively restrained by lateral motion in either direction. In effect then, the movement of the ankle in the opposed lateral directions of inversion and eversion is prevented by locking the brace in place. In effect, the upper parts of the brace arms 56, 58 are fixed in position by the laced up or otherwise fastened body 12 and the bottom portion 60 fixed by its being held by the posterior arch of the wearer's and its placement in the pocket 25. Thus by having a portion of the brace (further stiffened by reason of its incorporation into the body 12) forward of the ankle's pivoting points or axis of motion and another portion also further stiffened by incorporation into the body above the ankle's pivoting points, the effect of preventing or at least substantially reducing eversion and inversion is brought about. In essence, the effect is to pin the front of the foot to the lower leg as if by attaching a rigid angularly disposed stiff rod thereacross on both sides thereof without the obvious problems that such theoretical rods would cause.

Figure 10:
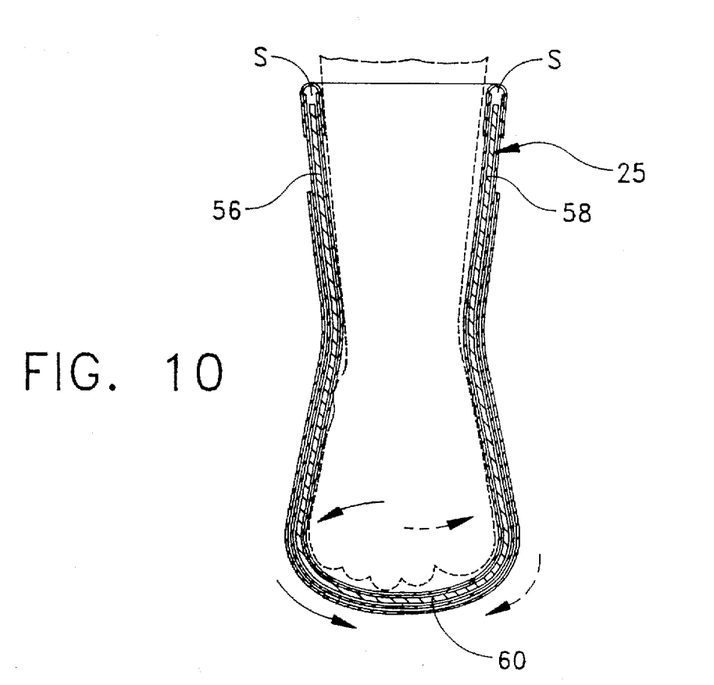
FIG. 10 is a partial sectional schematic view along line 10—10 of FIG. 3 of a brace attached to a right foot showing the manner in which forces against one side of the brace thereof are transmitted to and resisted by both sides of the brace.

The specific manner in which the brace functions to resist excess foot motion (inversion is specifically shown) is best illustrated by reference to schematic FIG. 10 in which brace arms 56, 58 connected by bottom portion 60 form the brace 50. Because of the inherent but limited flexibility of the brace, its arms better conform to the sides of the foot which action is also afforded by the flexible envelope. This close conformity of the brace to the foot achieves, in effect, what might be termed a cradling action where the foot is cupped and supported by the brace and, although permitting some inversion and eversion of the foot, limits such movement materially. This is in distinct contrast to a completely rigid system wherein any foot movement is prevented by the foot moving against an immovable and entirely non-flexible surface. The somewhat flexible nature of the brace also insures that this cradling effect is particularly present on the side of the foot opposite to the side of attempted movement, e.g., if inversion is attempted, the force against the medial side of the device and against brace arm 58 is also transmitted to the lateral side of the device via the brace and arm 56 so that the opposite side resists the turning movement of the foot by tightening up against the ankle joints on the lateral side and, in effect, cupping the foot in the brace such that excess motion and possible injury is prevented.

Figure 11:
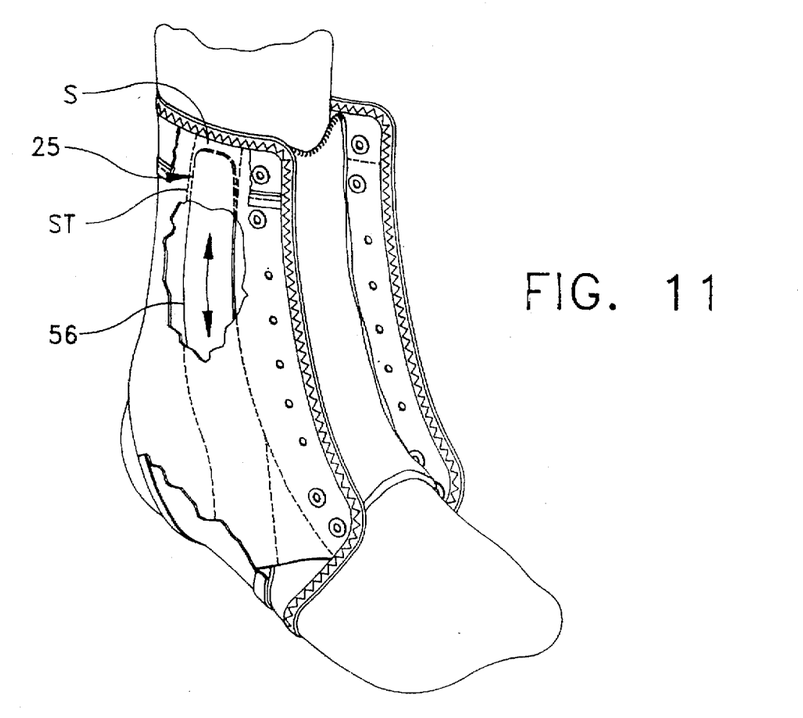
FIG. 11 is a perspective view similar to FIG. 1 but in which the stitched nature and extent of the pocket and the manner in which the brace held therein can move is best illustrated.

Also when inversion motion is attempted, the lateral side of the foot (left side in viewing the right foot from front as in FIG. 10) presses against the envelope in a downwardly leftwardly direction as shown by the arrow. The envelope being somewhat flexible tends to give a little and presses against arm 56. The resultant downward tension force is frictionally resisted by brace arm 56 being held in the pocket 25. The pocket, as previously indicated, is made up of those sections of the envelope in face to face position and between which the pocket 25 is formed in part by contact with the brace to create such friction as does the edges of the brace in contact with the pocket edges preferably formed by stitching the envelope sections together to closely follow the outline or shape of the brace (see stitching ST in FIG. 11). Also, it is desirable to leave a little space at the top of the pocket beyond which the top ends of the arms are disposed when the front is at rest within the support. This space S enables some back and forth movement or slippage of the brace within the pocket. The space S at the top of each pocket leg is in the order of ⅛ to ½ inch and is primarily to relieve any possible inward buckling of the brace against the foot when in use which could be painful.

The believed manner in which foot force is resisted and limited by the brace is that the upper part of brace arm 56 resists the downward tensional force by reason of its frictional relationship in the pocket while simultaneously some compression force is also imparted to the rest of the brace which also resists movement by its frictional relationship with the pocket. Some of the resistance to movement of the brace is also provided by the overall envelope by reason of the lacing which, in effect, provides some lateral squeezing force against both sides of the brace which also is believed to provide some resistance of movement for the brace. The forces above described would, of course, be reversed when eversion movement of the foot is attempted. One of the keys of the subject successful support is that it combines the comfort of a closely fitting envelope with the greater foot restraining features of more rigid supports. Thus by regulating the flexibility and rigidity of the brace and the frictional force by which it resists moving in the pocket, a support which allows some foot movement (inversion and eversion) but not to the full permitting extent is achieved. Thus any possible brace movement to the left as shown in FIG. 10 is resisted by the rest of the brace by this downward tension or pulling force upon the other brace arm via the connecting base portion which is, of course, resisted by the other brace arm in turn restrained by the pocket envelope, etc. This restraining force is even more pronounced when attempted inversion or eversion movement is coupled with a twisting or plantar flexion movement of the ankle. Also, the support because of the position of the brace 50 essentially forward of the malleoli, also controls inversion and eversion to a greater degree than prior art devices which generally are placed over the joint between the talus and the tibia and the talus and the calcaneous. The present U-shaped brace by its positioning essentially forward of the malleoli not only controls the motions between the above mentioned joints but also controls motion between the calcaneous and cuboid and the talus and the navicular joints. These features in combination with the brace placement essentially forward of the malleolii are believed to impart the desired range of foot mobility and restraint.

Obviously, the same effect could be accomplished if the brace was positioned even further forwardly with respect to the wearer's foot, but such placement would not only present an awkward position to be maintained but would also to some extent restrain the desired up and down flexion and function. Accordingly, it is best to place the brace adjacent to or in close approximation to both the lateral and medial malleolus but definitely at least partially forward of each to accomplish the desired result.

Figure 1:
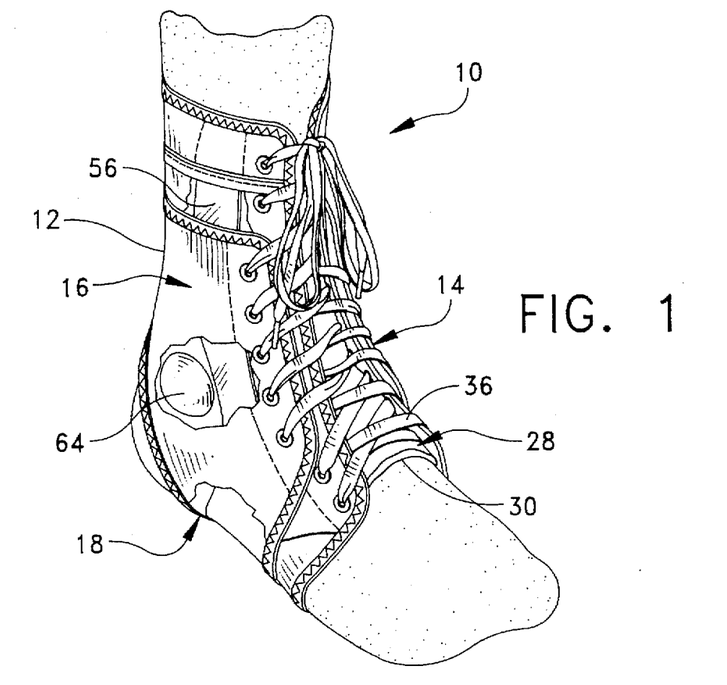
FIG. 1 is a perspective view of the support of the present invention in place on the wearer's foot.
Figure 2:
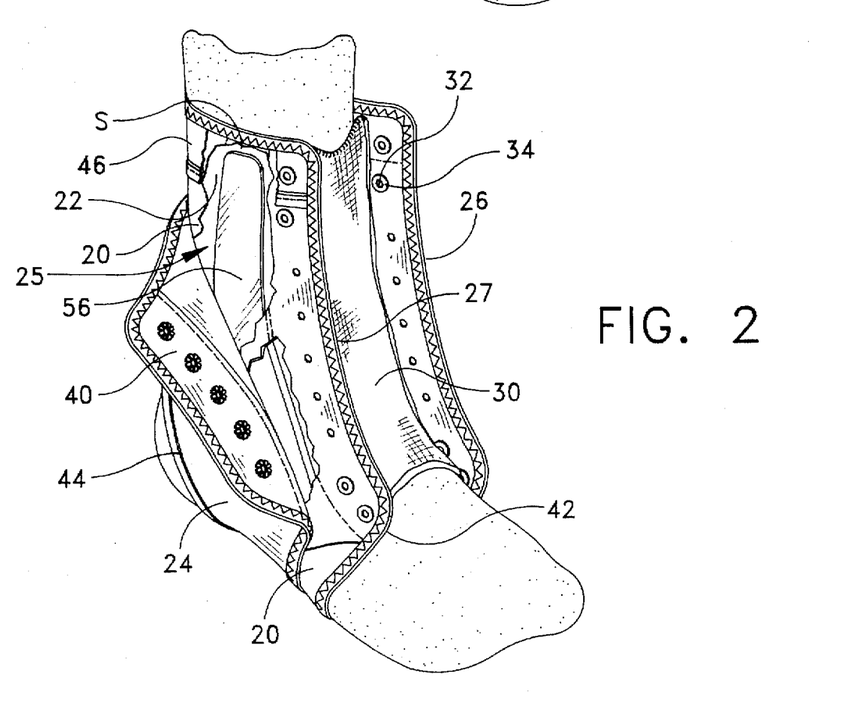
FIG. 2 is a perspective view similar to FIG. 1 but showing parts broken away and unlaced for clarity.
Figures 3, 4:
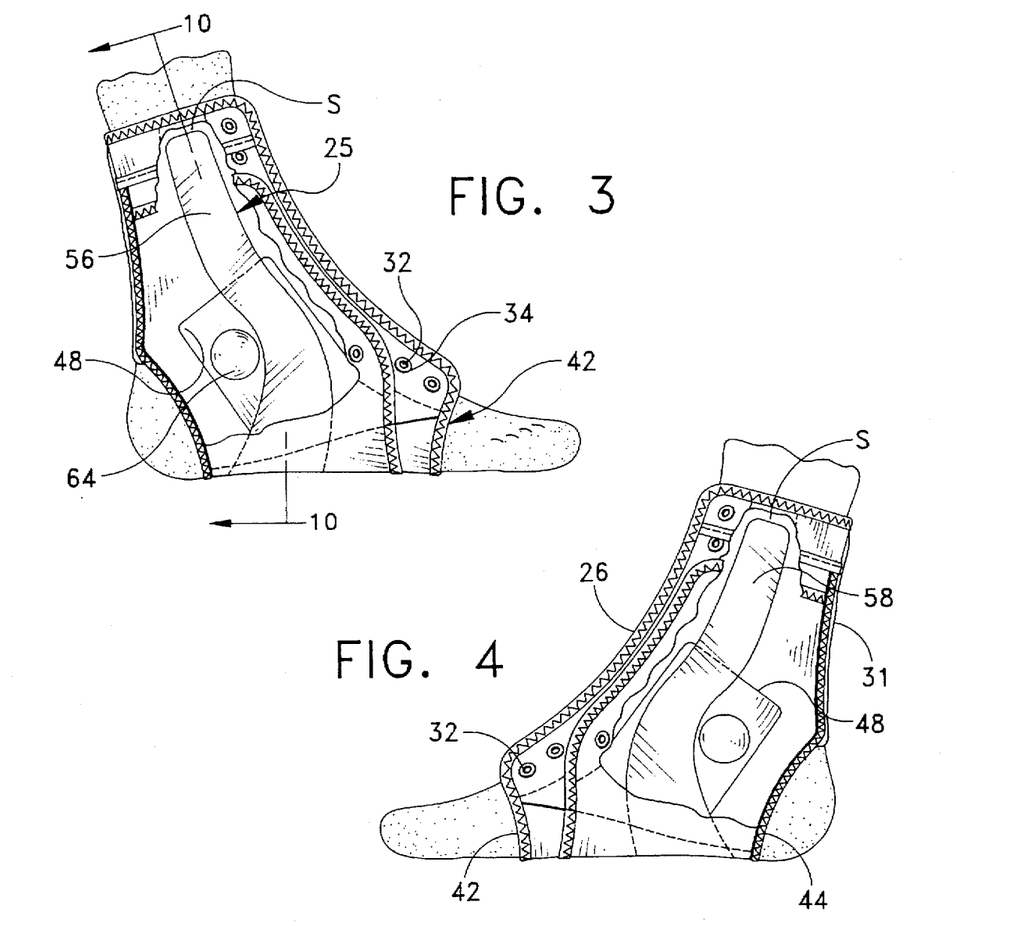
FIG. 3 is a side elevation view taken from the left side of FIG. 1.
FIG. 4 is a side elevation view taken from the right side of FIG. 1.
Figure 5:
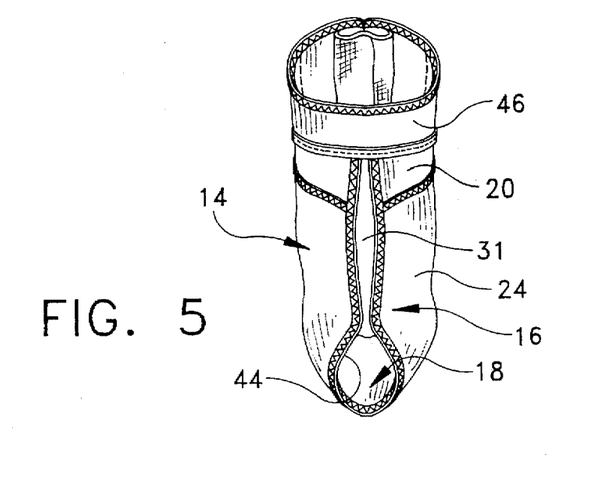
FIG. 5 is an elevation view taken from the rear.
Figure 6:
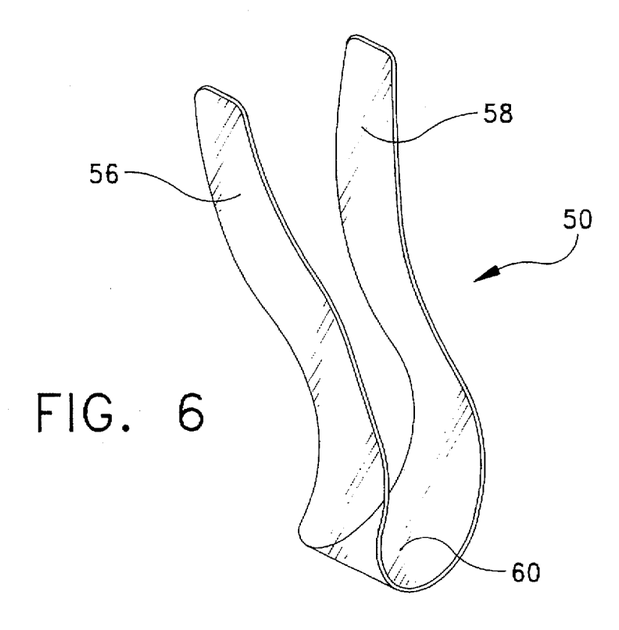
FIG. 6 is a perspective view of the brace portion of the support.
Figure 6A:
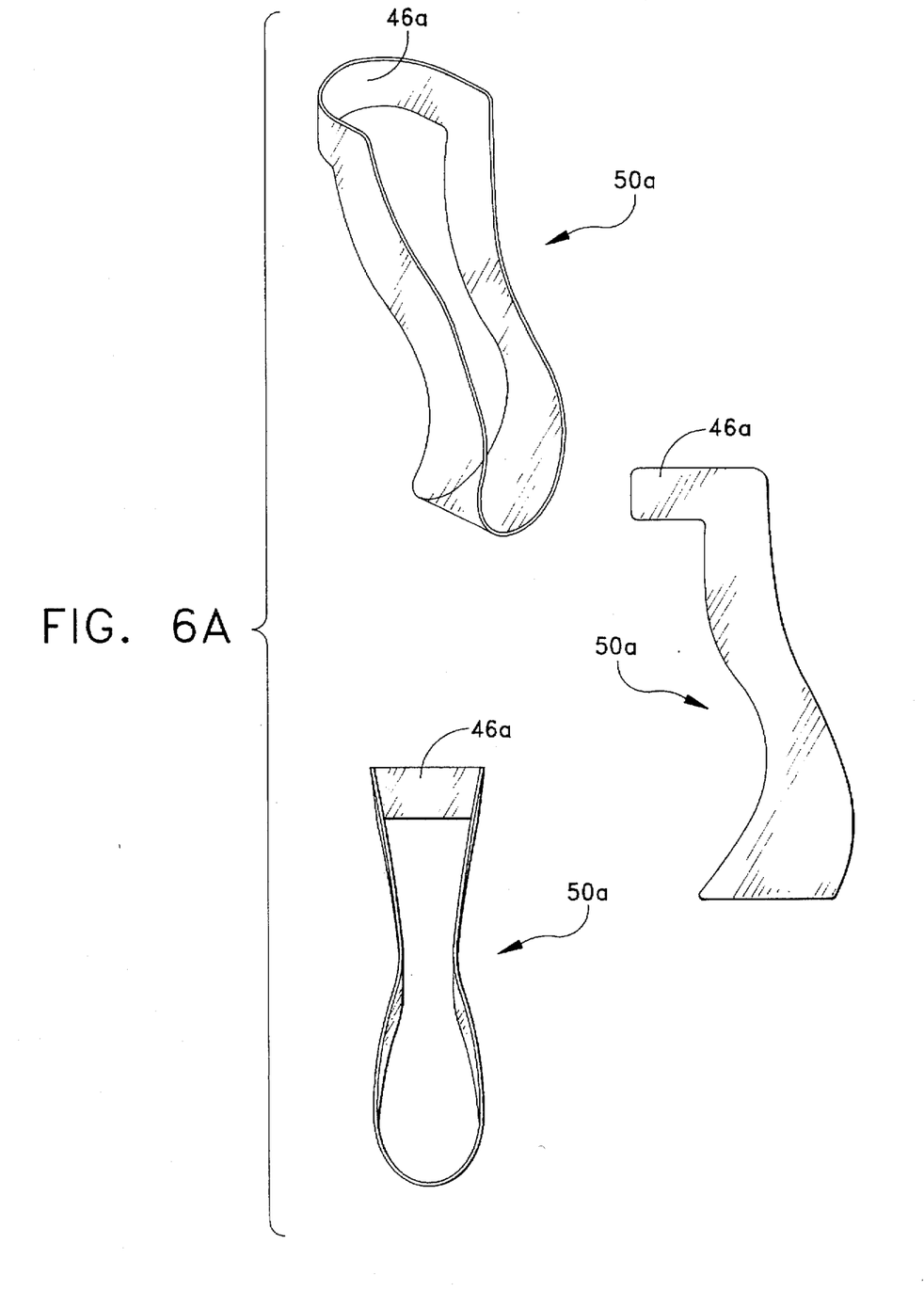
Figure 7:
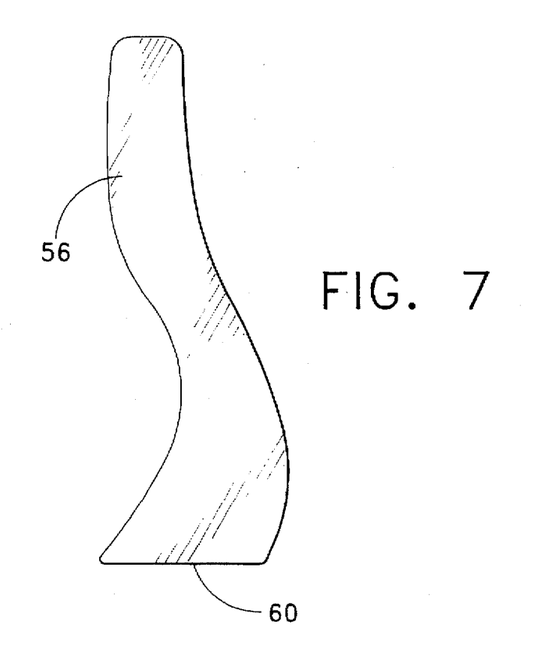
FIG. 7 is a left side elevation of FIG. 6.
Figure 8:
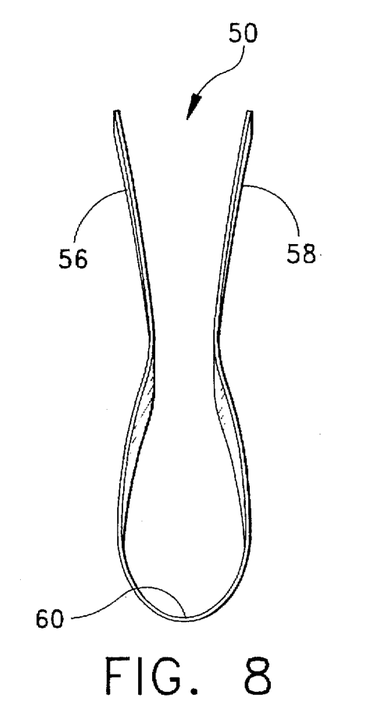
FIG. 8 is a front elevation of FIG. 6.

It is also possible to utilize a brace of modified form such as shown by reference numeral 50a of FIG. 6A. Such brace 50a utilizes the same overall configuration and for the same purposes as explained in relation to brace 50 but incorporates an integral bridge segment 46a to provide additional stiffness much in the same manner as bridge portion 46. The bridge segment 46a may be in place of or incorporated in addition to bridge 46 and would thus be positioned in pocket 25 for such purpose.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An ankle-joint support adapted to be worn over the foot of a human so as to support the ankle and ankle joint thereof, comprising a first member defining a flexible envelope and resultant foot receiving cavity and having a generally U-shaped body having a bottom and opposed sides adapted to fit around the bottom and opposed sides of the human foot and defining a toe opening at a front thereof and a heel opening at a rear thereof and a second member in the form of a one piece non-elastic, flexible yet relatively rigid generally U-shaped brace, said brace having a pair of upwardly rearwardly extending arms and an integral connecting base portion, said second member generally fixedly positioned with relation to said first member with said second member base portion positioned to conform to a portion of the envelope passing underneath the posterior arch of a wearer's foot with said arms upwardly extending from said base portion to points essentially forward of both the inner and outer malleolus of the wearer and means associated with said first member for releasably retaining said support on the ankle of the wearer.

2. The support of claim 1, wherein said first member having first and second sections disposed in face to face contact with each other and in part forming a pocket for the receipt and the generally fixed positioning of said brace with respect to said envelope.

3. The support of claim 2, wherein said means for releasably retaining said support on the wearer's ankle being a lace up system including a row of eyelets formed adjacent a forward edge of said opposed sides of said body in turn adapted to receive laces.

4. The support of claim 2, wherein said first member including a third outer section overlying a portion of said first section, said third section including rows of secondary eyelets at the forward edges thereof.

5. The support of claim 2, wherein said first member including added upper support means in the form of a separate material strip passing across the top of said opposed sides thereof at the heel thereof.

6. The support of claim 5, wherein said upper support means being a bridge integral with the arms of said brace and passing in back of the heel portion of said first member.

7. The support of claim 1, wherein said brace arms each upwardly extending to a first area generally forward of and generally vertically aligned with said malleoli and then rearwardly upwardly extending from said areas to a second area above and generally vertically aligned with said malleoli.

8. The support of claim 7, wherein said brace arms each upwardly forwardly extending to said first area.

9. The support of claim 1, wherein said brace being a thin-walled relatively stiff plastic sheet.

10. The support of claim 1, wherein said brace arms being relatively flexibly movable towards and away from each other when unsupported by said envelope.

* * * * *